United States Patent

Ueno et al.

[11] Patent Number: 6,001,896
[45] Date of Patent: Dec. 14, 1999

[54] ADHESIVE FOR DENTAL RESIN COMPOSITE MATERIALS

[75] Inventors: Takayuki Ueno, Tokyo; Tomohiro Kumagai, Kuki, both of Japan

[73] Assignee: GC Corporation, Tokyo, Japan

[21] Appl. No.: 09/010,856

[22] Filed: Jan. 23, 1998

Related U.S. Application Data

[63] Continuation of application No. 08/622,384, Mar. 27, 1996, Pat. No. 5,770,638.

[30] Foreign Application Priority Data

Apr. 5, 1995 [JP] Japan ................................. 7-103214

[51] Int. Cl.$^6$ .............................. A61K 6/00; A61C 13/23
[52] U.S. Cl. ......................... 523/116; 523/113; 524/533; 524/548; 524/549; 433/228.1
[58] Field of Search .................... 523/113, 116; 524/531, 548, 549; 433/228.1

[56] References Cited

U.S. PATENT DOCUMENTS

| | | |
|---|---|---|
| 4,820,744 | 4/1989 | Kubota et al. ..................... 523/116 |
| 5,270,350 | 12/1993 | Mueller et al. . |
| 5,389,699 | 2/1995 | Rehmer et al. . |
| 5,663,211 | 9/1997 | Kominami et al. ..................... 522/8 |
| 5,770,638 | 6/1998 | Ueno et al. ........................... 523/116 |

*Primary Examiner*—Andrew E. C. Merriam
*Attorney, Agent, or Firm*—Oblon, Spivak, McClelland, Maier & Neustadt, P.C.

[57] ABSTRACT

An adhesive for dental resin composite materials is disclosed, which comprises (a) from 10 to 40 parts by weight of tetrahydrofurfuryl methacrylate; (b) from 90 to 60 parts by weight of one or more methacrylates having at least one unsaturated double bond in one molecule thereof; and (c) from 0.04 to 0.12 part by weight, based on 100 parts by weight of the monomer mixture consisting of (a) and (b), of a photopolymerization initiator, the adhesive for dental resin composite materials of the present invention having a proper viscosity, not causing the color remaining, is superior in the operability and esthetics, having further a satisfactory adhesive strength, and is of safe even when used in the mouth.

6 Claims, No Drawings

ADHESIVE FOR DENTAL RESIN COMPOSITE MATERIALS

This application is a Continuation of application Ser. No. 08/622,384, filed on Mar. 27, 1996, now U.S. Pat. No. 5,770,638.

FIELD OF THE INVENTION

The present invention relates to an adhesive for dental resin composite materials which is used upon being newly applied with an unpolymerized acrylic resin composite material on a polymerized acrylic resin composite materials such as composite resins for crown and bridge and filling composite resins.

BACKGROUND OF THE INVENTION

Hitherto, in cases of dental restoration requiring the esthetics, restoration by dental prostheses such as resin jacket crowns, porcelain jacket crowns, resin facing crowns, and porcelain facing crowns, and restoration by filling with composite resins, have been widely employed. In particular, in recent years, since the resin capacity is greatly improved, restoration by resin facing crowns, or by filling with composite resins, which is easy in operation and inexpensive, is the main current in the restoration.

The resin facing crowns are produced by the operation in which tooth color resins called as composite resins for crown and bridge are applied on the surface of a crown and after forming the surface characterization, are polymerized and hardened. The application with the composite resins for crown and bridge is carried out by application with an opaque resin, application with a dentin resin, and application with an enamel resin, to thereby impart the surface characterization. In this case, the operation is carried out in such manner that primary polymerization (polymerization while retaining unpolymerized portions) is carred out at every stage of the application with an opaque resin, the application of a dentin resin, and the application with an enamel resin, and that when a prescribed surface characterization is completed, the applied resins are completely polymerized. However, since when such composite resins for crown and bridge are once completely polymerized, unpolymerized portions do not remain, the later applied composite resins for crown and bridge do not adhere but peel off and drop from the added portions. For this reason, it is substantially impossible to undergo forming the surface characterization after the resins have been once completely polymerized. When it is forced to undergo forming the surface characterization, an operation in which one layer of the surface of the polymerized and hardened resin is shaven off, and the resulting surface is coated with a radical polymerizable substance containing a polyfunctional (meth)acrylate, such as opaque liquids of composite resins for crown and bridge and dilute solutions of pastes for adjusting the shade, to again apply with a composite resin for crown and bridge, is employed. However, the adhesive strength in the added portions is at most about 60 kgf/cm$^2$ so that no satisfactory adhesive strength is obtained. In addition, the opaque liquids of composite resins for crown and bridge and the dilute solutions of pastes for adjusting the shade are so viscous that the shade of the photopolymerization initiator remains. Therefore, they can not be satisfied at all for use as an adhesive.

In cases of filling composite resins, the resins are filled in a tooth cavity in a mouth and after forming the surface characterization, are polymerized and hardened to undergo restoration. However, since no adhesive to strongly adhere the filling composite resins to each other is available, after the resins have been once completely polymerized, it is impossible to undergo additional filling for the purpose of forming the surface characterization. For this reason, operations for removing the filling composite resins filled and hardened in the tooth cavity and again undergoing filling were necessary.

Taking into consideration the present state that no adhesive for adhering dental resin composite materials such as composite resins for crown and bridge and filling composite resins to each other is present and that with the opaque liquids of composite resins for crown and bridge and the dilute solutions of pastes for adjusting the shade to be used as a substitute, not only a satisfactory adhesive strength is not obtained, but also the viscosity is high, the color remains, the operability and esthetics are not satisfactory, the present inventors had as their object to developing an exclusive adhesive for dental resin composite materials, which has a proper viscosity, which is free from the color remaining and is superior in the operability and esthetics, has a satisfactory adhesive strength, and which is safety even when it is used in the mouth.

SUMMARY OF THE INVENTION

In order to solve the above-described subject, the present inventors have made extensive investigations. As a result, they have successfully developed an adhesive for dental resin composite materials, in which the use of tetrahydrofurfuryl methacrylate having good wettability to the surface of the polymerized and hardened resin makes the monomers possibly enter into even minute unevennesses on the resin surface, to obtain an improved adhesive strength on account of an increase in the mechanical interlocking force, and which from the operability standpoint, not only has a proper viscosity so that upon coating, it is rapidly diffused onto the resin surface to obtain a good coating feeling, but also is free from the color remaining because the adhesive layer can be made thin, so that after polishing, the interfacial boundary is not noticeable, to thereby achieve superiority in the esthetics.

That is, the present invention provides an adhesive for dental resin composite materials, which comprises (a) from 10 to 40 parts by weight of tetrahydrofurfuryl methacrylate;
(b) from 90 to 60 parts by weight of one or more methacrylates having at least one unsaturated double bond in one molecule thereof; and
(c) from 0.04 to 0.12 part by weight, based on 100 parts by weight of the monomer mixture consisting of (a) and (b), of a photopolymerization initiator.

In order to increase the shelf stability of this composition, it is the usual way to compound it with a very small amount of a polymerization inhibitor.

DETAILED DESCRIPTION OF THE INVENTION

The respective components which are used in the present invention are now described in detail.

The tetrahydrofurfuryl methacrylate (a) has good wettability to the surface of the polymerized and hardened resin, enters into minute unevennesses on the resin surface, and effectively acts on the improvement in the adhesive strength on account of an increase in the mechanical interlocking force. Further, from the operability standpoint, it has a proper viscosity and provides an effect such that upon coating, it is rapidly diffused onto the resin surface. A suitable amount of the component (a) to be compounded is from 10 to 40 parts by weight based on 100 parts by weight of the monomer mixture consisting of (a) and (b). If the amount of the component (a) is less than 10 parts by weight, the viscosity of the resulting adhesive is so high that it is difficult to apply it, whereas if it exceeds 40 parts by weight, the adhesive strength of the adhesive rather decreases. In cases that a higher adhesive strength is required, it is desired that the amount of the component (a) is from 10 to 20 parts by weight. Incidentally, while tetrahydrofurfuryl acrylate having an analogous structure is effective in the adhesive force and wettability similar to tetrahydrofurfuryl methacrylate, since it is highly toxic and stimulative, it is not proper to use it in the intraoral circumstance.

The methacrylate (b) having at least one unsaturated double bond in one molecule thereof is a component that acts as a matrix in the adhesive components and keeps the strength of the adhesive itself. A suitable amount of the component (b) to be compounded is from 90 to 60 parts by weight based on the monomer mixture consisting of (a) and (b). If the amount of the component (b) exceeds 90 parts by weight, the viscosity of the resulting adhesive is so high that the operability decreases, whereas if it is less than 60 parts by weight, it is impossible to provide the adhesive itself with a satisfactory strength. Specific examples of the methacrylate having at least one unsaturated double bond in one molecule thereof include methyl methacrylate, ethyl methacrylate, isopropyl methacrylate, 2-hydroxyethyl methacrylate, 3-hydroxypropyl methacrylate, 2-hydroxy-1,3-dimethacryloxypropane, n-butyl methacrylate, isobutyl methacrylate, hydroxypropyl methacrylate, glycidyl methacrylate, 2-methoxyethyl methacrylate, 2-ethylhexyl methacrylate, benzyl methacrylate, 2,2-bis (methacryloxyphenhyl)propane, 2,2-bis[4-(2-hydroxy-3-methacryloxypropoxy)phenyl]propane, 2,2-bis(4-methacryloxydiethoxyphenyl)propane, 2,2-bis(4-methacryloxypolyethoxyphenyl)propane, ethylene glycol dimethacrylate, diethylene glycol dimethacrylate, triethylene glycol dimethacrylate, butylene glycol dimethacrylate, neopentyl glycol dimethacrylate, 1,3-butanediol dimethacrylate, 1,4-butanediol dimethacrylate, 1,6-hexanediol dimethacrylate, trimethylolpropane trimethacrylate, trimethylolethane trimethacrylate, pentaerythritol trimethacrylate, trimethylolmethane trimethacrylate, pentaerythritol tetramethyarylate, and methacrylates having a urethane bond in the molecule thereof. Also, di-2-methacryloxyethyl-2,2,4-trimethylhexamethylene dicarbamate and compounds represented by the following formula:

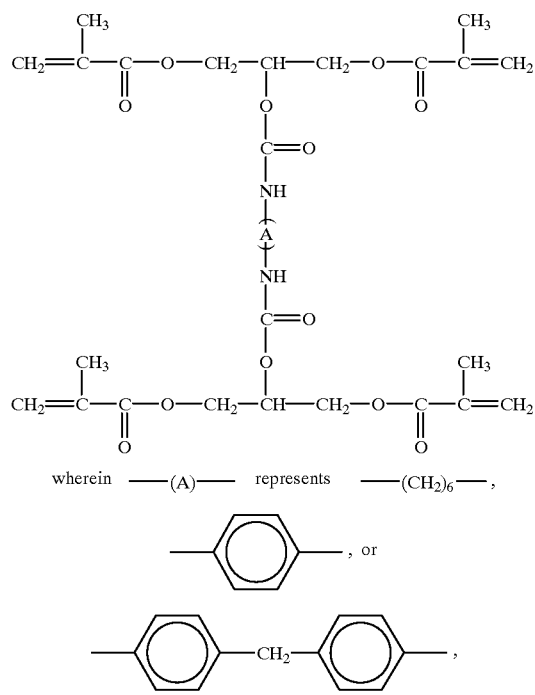

can be used. These methacrylates can be used alone or in admixture of two or more thereof, if desired.

The photopolymerization initiator (c) is the necessary component for hardening the adhesive. A suitable amount of the component (c) to be compounded is from 0.04 to 0.12 part by weight based on 100 parts by weight of the monomer mixture consisting of (a) and (b). If the amount of the component (c) is less than 0.04 part by weight, it takes an excessively long period of time to harden the resulting adhesive, whereas if it exceeds 0.12 part by weight, the adhesive tends to cause the color to remain. As the photopolymerization initiator, catalysts which comprise a combination of a sensitizer and a reducing agent and which is decomposed by visible light beams are used. Examples of the sensitizer include camphorquinone, benzil, diacetyl, benzyl dimethyl ketal, benzyl diethyl ketal, benzyl di(2-methoxyethyl) ketal, 4,4'-dimethylbenzyl-dimethyl ketal, anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropylthioxanthone, 2-nitrothioxanthone, 2-methylthioxanthone, 2,4-dimethylthioxanthone, 2,4-diethylthioxanthone, 2,4-diisopropylthioxanthone, 2-chloro-7-trifluoromethylxanthone, thioxanthone-10,10-dioxide, thioxanthone-10-oxide, 2,4,6-trimethylbenzoyldiphenylphosphine oxide, benzoin methyl ether, benzoin ethyl ether, isopropyl ether, benzoin isobutyl ether, benzophenone, bis(4-dimethylaminophenyl) ketone, 4,4'-bisdiethylaminobenzophenone, and amide group-containing compounds. Of these sensitizers, camphorquinone having an absorpition in a long wavelength region is preferred as a dental material. These sensitizers can be used alone or in admixture of two or more thereof.

As the reducing agent, tertiary amines and so on are generally used. Preferred examples of tertiary amines include N,N-dimethyl-p-toluidine, N,N-dimethylaminoethyl methacrylate, triethanolamine, methyl 4-dimethylaminobenzoate, ethyl 4-dimethylaminobenzoate, and isoamyl 4-dimethylaminobenzoate. Examples of other reducing agents include benzoyl peroxide, sodium sulfinate derivatives, and organometallic compounds. Of these reducing agents, ethyl 4-dimethylaminobenzoate and sodium benzenesulfinate are preferred because they are good in storage stability and do not cause yellowing. These reducing agents can be used alone or in admixture of two or more thereof, if desired.

The adhesive according to the present invention can achieve the polymerization reaction upon irradiation with visible light beams. As a light source of the visible light beams, light beams with a wavelength of from 350 to 800 nm, using halogen vapor lamps, xenon vapor lamps, high-pressure mercury vapor lamps, fluorescent tubes, and the like can be used.

The present invention is now described below in more detail with reference to the following Examples and Comparative Examples.

EXAMPLE 1

An adhesive for dental resin composite materials comprising:

| | |
|---|---|
| Tetrahydrofurfuryl methacrylate | 20 parts by weight |
| 1,3-Butanediol dimethacrylate | 40 parts by weight |
| Methyl methacrylate | 20 parts by weight |
| Di-2-methacryloxyethyl-2,2,4-trimethylhexamethylene dicarbamate | 20 parts by weight |
| Camphorquinone | 0.04 part by weight |
| Ethyl 4-dimethylaminobenzoate | 0.04 part by weight | was prepared and tested in terms of adhesive strength, cell toxicity, and wettability in the methods as described below. The results obtained are shown in Table 1.

EXAMPLES 2 TO 6

Adhesives for dental resin composite materials having a composition and compounding amounts as shown below were prepared and tested in the same manner as in Example 1. The results obtained are shown in Table 1.

EXAMPLE 2

| [EXAMPLE 2] | |
|---|---|
| Tetrahydrofurfuryl methacrylate | 20 parts by weight |
| Di-2-methacryloxyethyl-2,2,4-trimethylhexamethylene dicarbamate | 20 parts by weight |
| Triethylene glycol dimethacrylate | 40 parts by weight |
| Ethyl methacrylate | 20 parts by weight |
| Camphorquinone | 0.04 part by weight |
| Ethyl 4-dimethylaminobenzoate | 0.04 part by weight |
| [EXAMPLE 3] | |
| Tetrahydrofurfuryl methacrylate | 40 parts by weight |
| 2-Hydroxy-1,3-dimethacryloxy-propane | 20 parts by weight |
| 1,3-Butanediol dimethacrylate | 20 parts by weight |
| Methyl methacrylate | 20 parts by weight |
| Camphorquinone | 0.04 part by weight |
| Ethyl 4-dimethylaminobenzoate | 0.04 part by weight |
| [EXAMPLE 4] | |
| Tetrahydrofurfuryl methacrylate | 10 parts by weight |
| Di-2-methacryloxyethyl-2,2,4-trimethylhexamethylene dicarbamate | 20 parts by weight |
| Diethylene glycol dimethacrylate | 50 parts by weight |
| Ethyl methacrylate | 20 parts by weight |
| Camphorquinone | 0.04 part by weight |
| Ethyl 4-dimethylaminobenzoate | 0.04 part by weight |
| [EXAMPLE 5] | |
| Tetrahydrofurfuryl methacrylate3 | 30 parts by weight |
| Trimethylolpropane trimethacrylate | 25 parts by weight |
| 1,3-Butanediol dimethacrylate | 45 parts by weight |
| Camphorquinone | 0.04 part by weight |
| Ethyl 4-dimethylaminobenzoate | 0.04 part by weight |
| [EXAMPLE 6] | |
| Tetrahydrofurfuryl methacrylate | 20 parts by weight |
| Di-2-methacryloxyethyl-2,2,4-trimethylhexamethylene dicarbamate | 20 parts by weight |
| 1,3-Butanediol dimethacrylate | 40 parts by weight |
| Methyl methacrylate | 20 parts by weight |
| Camphorquinone | 0.05 part by weight |
| Sodium benzenesulfinate | 0.05 part by weight |

COMPARATIVE EXAMPLES 1 TO 4

Adhesives for dental resin composite materials having a composition and compounding amounts as shown below were prepared, except that the compounding amount of tetrahydrofurfuryl methacrylate as the necessary component in the present invention fell outside the scope of the present invention (Comparative Examples 1 and 2) and that tetrahydrofurfuryl acrylate was used in place of the tetrahydrofurfuryl methacrylate (Comparative Example 3), respectively, and tested in the same manner as in Example 1. Also, in Comparative Example 4, the same test as in Example 1 was carried out using an opaque liquid of a light-cured composite resin for crown and bridge ("Thermoresin LCII", a trade name of GC Corporation). The results obtained are shown in Table 2.

COMPARATIVE EXAMPLE 1

| [COMPARATIVE EXAMPLE 1] | |
|---|---|
| Tetrahydrofurfuryl methacrylate | 50 parts by weight |
| Di-2-methacryloxyethyl-2,2,4-trimethylhexamethylene dicarbamate | 20 parts by weight |
| 1,3-Butanediol dimethacrylate | 10 parts by weight |
| Methyl methacrylate | 20 parts by weight |
| Camphorquinone | 0.04 part by weight |
| Ethyl 4-dimethylaminobenzoate | 0.04 part by weight |
| [COMPARATIVE EXAMPLE 2] | |
| Tetrahydrofurfuryl methacrylate | 4 parts by weight |
| Di-2-methacryloxyethyl-2,2,4-trimethylhexamethylene dicarbamate | 20 parts by weight |
| Triethylene glycol dimethacrylate | 56 parts by weight |
| Ethyl methacrylate | 20 parts by weight |
| Camphorquinone | 0.04 part by weight |
| Ethyl 4-dimethylaminobenzoate | 0.04 part by weight |
| [COMPARATIVE EXAMPLE 3] | |
| Tetrahydrofurfuryl acrylate | 20 parts by weight |
| Di-2-methacryloxyethyl-2,2,4-trimethylhexamethylene dicarbamate | 20 parts by weight |
| Diethylene glycol dimethacrylate | 40 parts by weight |
| Ethyl methacrylate | 20 parts by weight |
| Camphorquinone | 0.04 part by weight |
| Ethyl 4-dimethylaminobenzoate | 0.04 part by weight |

Measurement of Adhesive Strength (1) Polymerization and hardening products having a disc-like shape (Φ15.0×3.0 mm) were prepared using a dentin paste of a light-cured composite resin for crown and bridge ("Thermoresin LCII", a trade name of GC Corporation) and a photo activating light ("LABOLIGHT LV-II", a trade name of GC Corporation) for the polymerization in cases of composite resins for crown and bridge and a light-cured restrative composite resin ("Estio LC", a trade name of GC Corporation) and a photo activating light ("GC New Light VL-II", a trade name of GC Corporation) for the polymerization in cases of filling composite resins, respectively and stored in water at 37° C. for one week to prepare adherends.

(2) The adherend surface was polished using a wet abrasive paper #1000, laminated with a vinyl tape having holes with a diameter of 3.0 mm on the surface thereof to make the area constant, coated with each of the adhesives of the Examples and Comparative Examples, and then irradiated with visible light beams for one minute by means of the photo activating lights.

(3) Onto the adhesive-coated adherend, each of the above-described light-cured composite resins for crown and bridge and filling composite resins was again applied and hardened upon irradiation with visible light beams to prepare specimens.

(4) The tensile adhesion test was carried out by immersing each specimen with water at 37° C. for one day and then drawn at a crosshead speed of 1.0 mm/min. by means of Autograph made by Shimadzu Corporation to measure the adhesive strength. The numerical values as shown in the tables are a mean value of the measured values with respect to the five specimens.

Cell Toxicity Test (1) Each of the adhesives prepared in the Examples and Comparative Examples was filled in an acrylic ring (inside diameter: 6 mm, height: 1 mm), a glass plate (thickness: 3 mm) was put thereon to make the height of the sample constant, and irradiation with a light was carried out for 60 seconds by means of a photo activating light to prepare samples. Each of the samples was immersed in a culture medium (Eagle's MEM) so as to have a rate of 565.49 to 6.28 $mm^2$/ml and extracted at 37° C. and at 100 rpm for 24 hours. The extracts thus obtained were provided for the following measurement.

(2) The measurement method was carried out in accordance with the Mosmann MTT assay method. That is, HeLa 3 cells ($2 \times 10^5$ cell/ml) in the exponential growth phase were sworn on a 12-punched multi-plate in an amount of 1 ml, respectively, and after cultivation for 24 hours (at 37° C. and at a humidity of 100%), the culture medium was collected off, and 1 ml of each of the extracts having various concentrations was administered.

(3) After cultivation for 24 hours (at 37° C. and at a humidity of 100%) and observation of the cell shapes, 0.1 ml of the MTT solution (MTT: 0.5 mg/ml-PBS) was added. After cultivation for an additional 4 hours, 1.5 ml of an acid-isopropanol (0.4N HCl-isopropanol) was added to stop the reaction.

(4) Absorbances at wavelengths of 570 nm and 630 nm were measured by means of a multi-plate recorder (MTP 32, made by Corona Co., Ltd.) to obtain relative numbers of cells, and extraction concentrations ($ID_{50}$ values) of samples to show a relative number of cells of 50% were compared.

Measurement of Wettability (1) A dentin paste of a light-cured composite resin for crown and bridge ("Thermoresin LCII, a trade name of GC Corporation) was used as a dental resin composite material, and a photo activating light ("LABOLIGHT LV-II", a trade name of GC Corporation) was used for the polymerization to prepare hardening products in a disc-like shape (Φ20.0× 2.0 mm), the surfaces of which were then subjected to a mirror polishing using alumina having a particle size of 30 μm.

(2) The polished surface of the hardening product was kept horizontal, in a center of which was then added dropwise one drop (about 0.025 ml) of each of the adhesives prepared in the Examples and Comparative Examples. After allowing to stand for 10 seconds, the spread diameters were measured.

(3) The wettability was evaluated on a scale of the following four grades based on the size of the spread diameter.

a: The spread diameter reached 20 mm (over the whole surface).

b: The spread diameter was 15 mm or more but less than 20 mm.

c: The spread diameter was 10 mm or more but less than 15 mm.

d: The spread diameter was less than 10 mm.

TABLE 1

| Example No. | Adhesive Strength (kgf/cm$^2$) | | Cell Toxicity ($ID_{50}$) | Wetta- bility |
|---|---|---|---|---|
| | Composite resin for crown and bridge | Filling composite resin | | |
| 1 | 107.4 | 101.6 | 190 | a |
| 2 | 106.8 | 97.5 | 195 | b |
| 3 | 89.5 | 85.2 | 170 | a |
| 4 | 107.2 | 100.9 | 205 | b |
| 5 | 97.2 | 91.3 | 185 | b |
| 6 | 128.3 | 111.8 | 187 | b |

TABLE 2

| Example No. | Adhesive Strength (kgf/cm$^2$) | | Cell Toxicity ($ID_{50}$) | Wetta- bility |
|---|---|---|---|---|
| | Composite resin for crown and bridge | Filling composite resin | | |
| 1 | 77.8 | 72.4 | 179 | a |
| 2 | 73.4 | 68.7 | 188 | c |
| 3 | 114.7 | 105.8 | 67 | b |
| 4 | 67.9 | 62.4 | 169 | d |

As is clear from the results as shown in Tables 1 and 2, the adhesives of the respective Examples had a markedly superior adhesive strength as compared with the conventional opaque liquid of composite resin for crown and bridge and the dilute solution of the paste for adjusting the shade as well as were superior in the operability such that the evaluation of the wettability was on either a grade a or b and could be very easily coated. Also, with respect to the cell toxicity test, the adhesives of the respective Examples exhibited high $ID_{50}$ values and were superior in the bio-compatibility and hence, could be confirmed that they could be used with confidence even in the mouth. In the case of Comparative Example 1 in which the amount of the tetrahydrofurfuryl methacrylate compounded was too much, it was confirmed that the adhesive strength became low. In the case of Comparative Example 2 in which the amount of the tetrahydrofurfuryl methacrylate compounded was too small, not only the adhesive strength was not satisfactory, but also the evaluation of the wettability was on a grade c so that a satisfactory wetting was not generated for minute and complicated shapes as in dental protheses or restorations. Thus, it was confirmed that the adhesive of Comparative Example 2 was hardly applied for the clinical use. In the case of Comparative Example 3 in which tetrahydrofurfuryl acrylate was used, while the adhesive strength and wettability were satisfactory, the $ID_{50}$ value in the cell toxicity test was so low that it was confirmed that the adhesive of Comparative Example 3 could not be used in the mouth. In the case of Comparative Example 4 in which the opaque liquid of composite resin for crown and bridge was used as the adhesive, not only the adhesive strength was low, but also the evaluation of the wettability was very inferior grade d being.

While the invention has been described in detail and with reference to specific embodiments thereof, it will be apparent to one skilled in the art that various changes and modifications can be made therein without departing from the spirit and scope thereof.

An adhesive for dental resin composite materials according to the present invention uses tetrahydrofurfuryl methacrylate having a good wettability to the surface of the polymerized and hardened resin making the monomers possibly enter into even minute unevennesses on the resin surface to obtain an improved adhesive strength on account of an increase in the mechanical interlocking force and is superior in the bio-compatibility and hence could be used with confidence for the dental protheses or restorations. Further from the operability standpoint, it possesses a proper viscosity so that it may rapidly diffuse onto the resin surface and is free from the color remaining because the adhesive layer can be made thin thereby achieve superiority in the esthetics. Thus it has made possible for the dentists to additionally apply composite resins for crown and bridge or filling composite resins with confidence achieving a remarkable contribution to the dental treatment.

What is claimed is:

1. An adhesive for dental resin composite materials, which comprises:
    (A) from about 10 to 40 parts by weight of tetrahydrofurfuryl methacrylate;
    (B) from about 90 to 60 parts by weight of one of more multi-functional methacrylates; containing two or more methacryloyl groups; and
    (C) from about 0.04 to 0.12 parts by weight, based on 100 parts by weight of the monomer mixture consisting of (A) and (B), of a photopolymerization initiator.

2. The adhesive of claim 1, wherein the photopolymerization initiator is a combination of a sensitizer and a reducing agent.

3. The adhesive of claim 1, which contains from 10 to 20 parts by weight of tetrahydrofurfuryl methacrylate.

4. The adhesive of claim 2, wherein the reducing agent is a tertiary amine selected from the group consisting of N,N-dimethyl-p-toluidine, N,N-dimethylaminoethyl methacrylate, triethanolamine, methyl-4-dimethylamino benzoate, ethyl 4-dimethylamino benzoate and isoamyl 4-dimethylamino benzoate.

5. The adhesive of claim 2, wherein said reducing agent is selected from the group consisting of ethyl 4-dimethylamino benzoate and sodium sulfinate.

6. The adhesive of claim 1, wherein said one or more methacrylates containing two or more methacryloyl groups are selected from the group consisting of 2,2-bis (methacryloxyphenyl) propane, 2,2-bis(4-(2-hydroxy-3-methacryloxy-propoxy) phenyl) propane, 2,2-bis(4-(2-hydroxy-3-methacryloxy-propoxy) phenyl) propane, 2,2-bis (4-methacryloxydiethoxyphenol) propane, 2,2-bis (4-methacryloxypolyethoxyphenyl) propane, ethylene glycol dimethacrylate, diethylene glycol dimethacrylate, triethylene glycol dimethacrylate, butylene glycol dimethacrylate, neopentyl glycol dimethacrylate, 1,3-butanediol dimethacrylate, 1,4-butane diol dimethacrylate, 1,6-hexanediol dimethacrylate, trimethylol propane trimethacrylate, trimethylol ethane trimethacrylate, and trimethylol methane trimethacrylate.

* * * * *